US009427161B2

(12) United States Patent
Vijayvergia et al.

(10) Patent No.: US 9,427,161 B2
(45) Date of Patent: Aug. 30, 2016

(54) CURVED PASSIVE ACOUSTIC DRIVER FOR MAGNETIC RESONANCE ELASTOGRAPHY

(71) Applicant: Northwestern University, Evanston, IL (US)

(72) Inventors: Mayank Vijayvergia, Lake Worth, FL (US); Gaurav Gadodia, Atlanta, GA (US); Sumeeth Jonathan, Manalapan, NJ (US); Samantha By, Katy, TX (US); Frank Miller, Chicago, IL (US); Timothy Carroll, Chicago, IL (US); Teresa Woodruff, Chicago, IL (US)

(73) Assignee: Northwestern University, Evanston, IL (US)

( * ) Notice: Subject to any disclaimer, the term of this patent is extended or adjusted under 35 U.S.C. 154(b) by 353 days.

(21) Appl. No.: 13/948,977

(22) Filed: Jul. 23, 2013

(65) Prior Publication Data

US 2014/0024922 A1    Jan. 23, 2014

Related U.S. Application Data

(60) Provisional application No. 61/674,586, filed on Jul. 23, 2012.

(51) Int. Cl.
*A61B 5/055* (2006.01)
*A61B 5/00* (2006.01)

(52) U.S. Cl.
CPC ........... *A61B 5/0035* (2013.01); *A61B 5/0051* (2013.01); *A61B 5/055* (2013.01)

(58) Field of Classification Search
CPC .......... G01R 33/56358; A61B 5/0035; A61B 5/0051; A61B 5/055
USPC ................................................. 600/411, 415
See application file for complete search history.

(56) References Cited

U.S. PATENT DOCUMENTS

| 4,350,847 A | 9/1982 | Polk |
| 2005/0104588 A1* | 5/2005 | Sinkus et al. ................. 324/309 |

(Continued)

OTHER PUBLICATIONS

University of Chicago, Computation Institute, Factors Affecting the Signal-to-Noise Ratio [online], Dec. 17, 2006, [retrieved on Dec. 6, 2013]. Retrieved from the internet: <URL:http://wiki.ci.uchicago.edu/pub/HNL/DifficultQuestion/howdoesmriwork.pdf>, p. 37.

(Continued)

*Primary Examiner* — Ruth S Smith
(74) *Attorney, Agent, or Firm* — Klintworth & Rozenblat IP LLC

(57) ABSTRACT

An acoustic driver system includes an active acoustic driver and a passive acoustic driver. The active acoustic driver is configured to produce oscillating acoustic energy. The passive acoustic driver is acoustically connected to the active acoustic driver and is configured to receive the oscillating acoustic energy and to convert it into shear waves. The passive acoustic driver includes a housing member and a vibrating member. The housing member includes a housing member cavity. The vibrating member is disposed at least partially within the housing member cavity. The vibrating member permanently retains a curved shape while disposed within the housing member cavity.

44 Claims, 7 Drawing Sheets

(56) References Cited

U.S. PATENT DOCUMENTS

| | | |
|---|---|---|
| 2005/0227364 A1 | 10/2005 | Madsen |
| 2006/0012367 A1* | 1/2006 | Meaney et al. ............... 324/315 |
| 2006/0264736 A1* | 11/2006 | Ehman et al. ................ 600/410 |
| 2008/0130937 A1 | 6/2008 | Perkins |
| 2009/0048544 A1* | 2/2009 | Rybyanets ........................ 601/2 |
| 2009/0295387 A1* | 12/2009 | Ehman et al. ................ 324/309 |
| 2009/0299168 A1 | 12/2009 | Ehman |
| 2011/0130660 A1 | 6/2011 | Cloutier |

OTHER PUBLICATIONS

International Search Report and Written Opinion from PCT/US13/51710, mailed Dec. 20, 2013, 13 pages.

* cited by examiner

CURVED PASSIVE ACOUSTIC DRIVER FOR MAGNETIC RESONANCE ELASTOGRAPHY

CROSS REFERENCE TO RELATED APPLICATIONS

The present application claims the benefit of U.S. Provisional Patent Application No. 61/674,586, filed Jul. 23, 2012. The content of this U.S. Provisional Patent Application is hereby incorporated by reference in its entirety.

STATEMENT REGARDING FEDERALLY SPONSORED RESEARCH OR DEVELOPMENT

This invention was made with government support under Grant No. NIH U54 HD041857 awarded by the National Institutes of Health. The government has certain rights in the invention.

FIELD OF THE DISCLOSURE

The disclosure relates to curved passive acoustic drivers for use in magnetic resonance elastography.

BACKGROUND OF THE DISCLOSURE

Magnetic resonance elastography (MRE) combines magnetic resonance imaging (MRI) with sound waves to create a visual map, or elastogram, of the stiffness or elasticity of human tissue. The examining physician has traditionally evaluated "tissue stiffness" through palpation. This method is limited to organs that are superficial and is subject to the skill of the physician. MRE provides a means to: examine large anatomic regions at greater depths; quantify the stiffness allowing for cross-sectional comparison of disease severity and longitudinal comparison of an individual's disease progression or regression; and provide a 3D image of stiffness so the relationship to surrounding organs and vasculature can be incorporated into treatment (i.e. surgical or radiotherapeutic) planning. Currently, technology is being clinically applied to detect the hardening of the liver in order to diagnose diseases such as liver fibrosis and cirrhosis. Existing technology typically uses a flat passive acoustic driver to deliver low-frequency acoustic waves from an active driver to the patient. Flat passive acoustic drivers are adequate to vibrate a large and superficial liver, but have been found to be ineffective at penetrating through the entire human abdomen. In particular, flat passive acoustic drivers have difficulty detecting cancer and other disease states with high enough accuracy in small, deep organs including the kidneys, ovaries, and pancreas. MRE as a technology is less than 10 years old, and much of the previous development work has been focused in MRI pulse sequence development and image reconstruction algorithms. Very little attention has been devoted to the optimization of acoustic drivers.

There is a need for an improved acoustic passive driver design which will improve the stiffness images produced using MRE to broaden the number of clinical applications of this technology to detect cancer or other diseases in small, deep organs or in other portions of the patient's body

SUMMARY OF THE DISCLOSURE

In one embodiment, a passive acoustic driver includes a housing member and a vibrating member. The housing member includes a housing member cavity. The vibrating member is disposed at least partially within the housing member cavity. The vibrating member permanently retains a curved shape while disposed within the housing member cavity.

In another embodiment, an acoustic driver system includes an active acoustic driver and a passive acoustic driver. The active acoustic driver is configured to produce oscillating acoustic energy. The passive acoustic driver is acoustically connected to the active acoustic driver and is configured to receive the oscillating acoustic energy and to convert it into shear waves. The passive acoustic driver includes a housing member and a vibrating member. The housing member includes a housing member cavity. The vibrating member is disposed at least partially within the housing member cavity. The vibrating member permanently retains a curved shape while disposed within the housing member cavity.

In an additional embodiment, a method of transmitting shear waves into a patient for magnetic resonance elastography is disclosed. In one step, a passive acoustic driver is disposed against a patient. The passive acoustic driver includes a housing member and a vibrating member. The housing member includes a housing member cavity. The vibrating member is disposed at least partially within the housing member cavity. The vibrating member permanently retains a curved shape while disposed within the housing member cavity. In another step, oscillating acoustic energy is transmitted from an active acoustic driver to the passive acoustic driver disposed against the patient. In still another step, the oscillating acoustic energy is converted into shear waves and the shear waves are transmitted into the patient with the passive acoustic driver.

These and other features, aspects and advantages of the disclosure will become better understood with reference to the following drawings, description and claims.

DETAILED DESCRIPTION OF THE DISCLOSURE

The following detailed description is of the best currently contemplated modes of carrying out the disclosure. The description is not to be taken in a limiting sense, but is made merely for the purpose of illustrating the general principles of the disclosure, since the scope of the disclosure is best defined by the appended claims.

Figure 1:
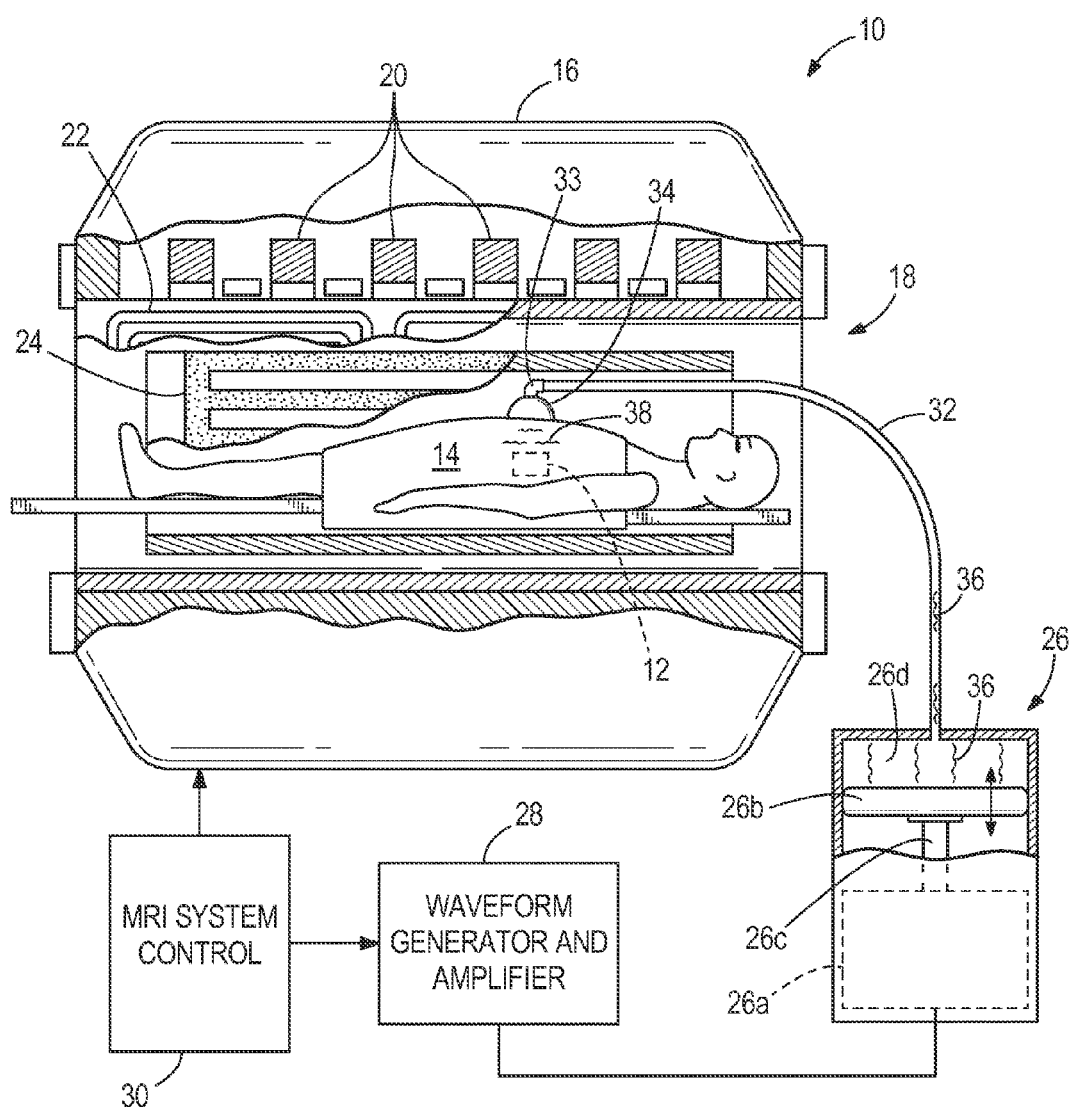
FIG. 1 is a pictorial representation of one embodiment of a system which can be used to conduct magnetic resonance imaging (MRI) and magnetic resonance elastography (MRE) to image an area of interest in a patient.

FIG. 1 is a pictorial representation of one embodiment of a system 10 which can be used to conduct magnetic resonance imaging (MRI) and magnetic resonance elastography (MRE) to image an area of interest 12 in a patient 14. In other embodiments, the system 10 may be used with other types of imaging devices. The area of interest 12 being imaged may comprise anything internal within the patient 14 such as any type of tissue including organs, bone, muscle, or other internal portions of the patient 14. The system 10 comprises an MRI system magnet 16, a shaft 18, a polarizing coil 20, gradient coils 22, an RF coil 24, an active acoustic driver 26, a waveform generator and amplifier 28, a MRI system control 30, a tube 32, an elbow joint 33, and a passive acoustic driver 34. In use, the patient 14 lies within the shaft 18 of the MRI system magnet 16 where the patient 14 is subjected to magnetic fields produced by the polarizing coil 20, the gradient coils 22, and the RF coil 24 while MR data is collected regarding the area of interest 12 of the patient 14. The active acoustic driver 26 is disposed remotely away from the magnet 16 and the passive acoustic driver 34 to avoid interference between the active acoustic driver 26 and the magnet 16. The active acoustic driver 26 is driven by the waveform generator and amplifier 28 which is controlled by a pulse sequencer in the MRI system control 30.

The active acoustic driver 26 includes a motor 26a, a diaphragm 26b, a drive rod 26c, and an acoustical chamber 26d. The motor 26a converts an alternating current from the waveform generator and amplifier 28 into a reciprocating linear motion which is translated by the drive rod 26c to the attached diaphragm 26b located within the acoustical chamber 26d to produce oscillating acoustic energy 36 (i.e. pressure waves) within the acoustical chamber 26d. The magnitude and frequency of the oscillating acoustic energy 36 is controlled by the waveform generator and amplifier 28 which controls the magnitude and frequency of the diaphragm 26 displacement. The tube 32 is attached between the active acoustic driver 26 and the passive acoustic driver 34, via the elbow joint 33, acoustically connecting the active acoustic driver 26 to the passive acoustic driver 34. The active acoustic driver 26 transmits the oscillating acoustic energy 36 in the form of longitudinal waves through the tube 32 and elbow joint 33 to the passive acoustic driver 34 which is attached to the patient 14 over the area of interest 12. In one embodiment, the transmitted oscillating acoustic energy 36 may comprise a frequency ranging between 40 to 100 Hz. In other embodiments, the frequency may vary.

The passive acoustic driver 34 does not require an electric current to operate, is made of materials which will not disturb the magnetic fields of the system 10, and can be attached to the patient 14 anywhere within the shaft 18 of the system 10 in any position, direction, or configuration. The passive acoustic driver 34 receives the oscillating acoustic energy 36, is energized by the oscillating acoustic energy 36, converts the longitudinal waves into shear waves 38 via mode conversation, and transmits the shear waves 38 into the patient 14 to the area of interest 12. The MRI system control 30 controls the system 10 to perform an MRE scan by driving the RF coil 24 and the gradient coils 22 in the magnet 16 to perform a series of pulse sequences while directing the waveform generator and amplifier 28 to apply an oscillatory stress to the patient 10 at the appropriate moment during each pulse sequence.

The system 10 may measure the properties of the area of interest 12 within the patient 14 using MRE. During this process the oscillatory stress is applied to the area of interest 12 and the resultant strain on the area of interest 12 is observed. By measuring the resultant strain of the area of interest 12, the elastic properties of the area of interest 12 may be calculated. When the oscillatory stress is applied in all three dimensions to the area of interest 12 and the resultant strain on the area of interest 12 is measured, the elastic properties of the area of interest 12 may be determined. By observing the rate at which the strain in the area of interest 12 decreases as a function of distance from the location of the oscillatory stress being applied, the attenuation of the strain wave may be estimated which in turn allows for the estimation of the viscous properties of the area of interest 12. The dispersion properties of the area of interest 12 may be estimated by observing the speed and attenuation of the strain waves as a function of their frequency. By using the system 10, a wide variety of properties (such as elasticity, stiffness, hardness, etc.) of the area of interest 12 of the patient 14 may be determined to allow a physician to determine and diagnose the condition or a disease of the area of interest 12 based on the determined condition or properties.

Figure 2:
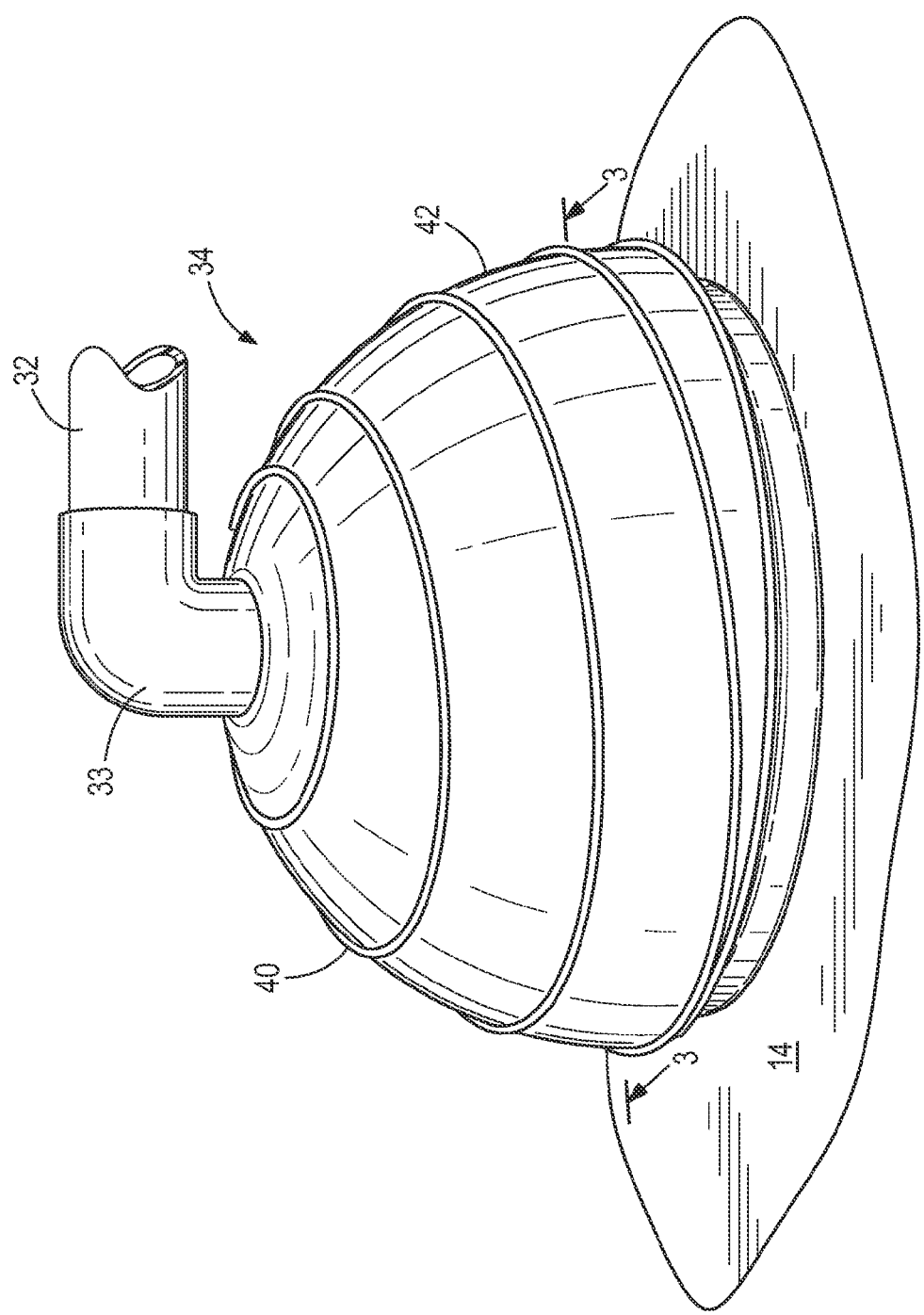
FIG. 2 illustrates a perspective view of one embodiment of a passive acoustic driver of the system of FIG. 1 disposed against and attached to a patient.
Figure 3:
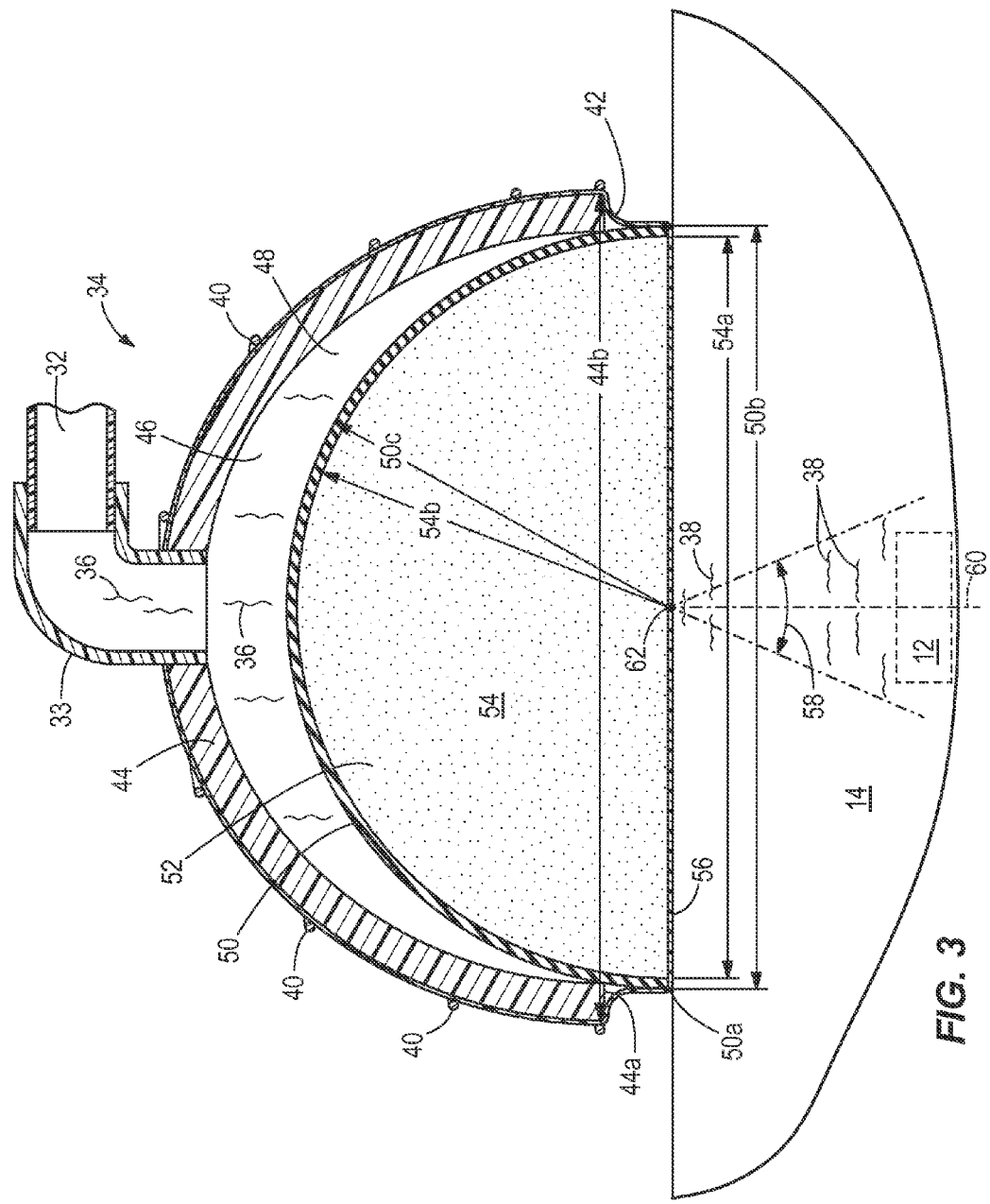
FIG. 3 illustrates a cross-section through line 3-3 of the passive acoustic driver of FIG. 2.

FIG. 2 illustrates a perspective view of one embodiment of the passive acoustic driver 34 of the system 10 of FIG. 1 disposed against and attached to a patient 14. FIG. 3 illustrates a cross-section through line 3-3 of the passive acoustic driver 34 of FIG. 2. As shown collectively in FIGS. 2 and 3, the passive acoustic driver 34 comprises the tube 32, a coil 40, a cover member 42, a housing member 44 comprising a housing member cavity 46, air 48, a vibrating member 50 comprising a vibrating member cavity 52, and a gel member 54. The tube 32 delivers the oscillating acoustic energy 36, transmitted from the active acoustic driver 26 of FIG. 1, in the form of longitudinal waves through the tube 32 into the housing member cavity 46 of the passive acoustic driver 34. In one embodiment, the transmitted oscillating acoustic energy 36 may comprise a frequency ranging between 40 to 100 Hz. In other embodiments, the frequency may vary. The tube 32 may be made of a wide variety of flexible tubing materials such as rubber, plastics including nylon, PVC (vinyl), polyethylene, and polyurethane (i.e. the Tygon brand), or other tubing materials. The elbow joint 33 may be made of an inflexible, non-metallic material such as PVC piping, hard plastic materials, or other types of materials.

The coil 40 is disposed around the housing member 44. The coil 40 increases a signal to noise ratio in the system 10 of FIG. 1 taking MRI images of the patient 14. The coil 40 is made of copper but in other embodiments may be made of a wide variety of materials such as any conductive, non-magnetic material such as titanium, aluminum, or another type of material. The cover member 42 is attached to the housing member 44 and covers the housing member 44, including end 44a of the housing member 44, and the vibrating member 50, including end 50a of the vibrating member, to form an air tight seal between the housing member 44 and the vibrating member 50. The cover member 42 is made of plastic (PVdC or LDPE) wrap but in other embodiments may be made of a wide variety of thin, non-metallic, airtight materials, or differing materials. The cover member 42 is attached to the housing member 44 using an adhesive such as epoxy, another plastic-to-plastic, non-metallic adhesive, or another type of material. The housing member 44 may be a curved shape such as hemispherical, elliptical, or another curved shape. In other embodiments, the shape of the housing member 44 may vary. The housing member 44 may be made of acrylic but in other embodiments may be made of a wide variety of inflexible, shape-retaining, non-metallic materials including plastics such as polyethylene, polypropylene, PVC, or other types of materials. The housing member 44 may comprise a diameter 44b ranging between 4 to 10 inches (~10 to 25 centimeters), the primary constraint being that it must have a diameter at least 0.5 inches (~1 cm) larger than that of the vibrating member 50. In a preferred embodiment, the diameter 44b is 5.5 inches (~14 centimeters). In other embodiments, the housing member 44 may vary in size.

The vibrating member 50 is disposed at least partially within the housing member cavity 46 of the housing member 44 between the housing member 44 and the cover member 42. The vibrating member 50 permanently retains a curved shape while disposed within the housing cavity 46. The vibrating member 50 may be made of plastic wrap, or other thin, hollow, non-metallic, appropriately shaped materials that may hold the gel member 54 such as rubber, varying types of plastic, or other materials. The curved shape may comprise a hemispherical shape, an elliptical shape, or another curved shape. The vibrating member 50 may comprise a diameter 50b ranging between 3 to 9 inches (~8 to 23 centimeters). In one embodiment, the curved shape may comprise a radius of curvature 50c of up to one-half of the diameter 44b of the housing member 44. In a preferred embodiment, the diameter 50b is 5 inches (~12.7 cm) and the radius of curvature 50c is 2.5 inches (~6.35 cm). In another embodiment, the curved shape may comprise a radius of curvature 50c ranging between 1.5 to 4.5 inches (~4 to 12 centimeters). In other embodiments, the size or the curvature of the vibrating member 50 may vary.

The air 48 is disposed between the housing member 44 and the vibrating member 50 with the cover member 42 providing the air tight seal between the housing member 44 and the vibrating member 50. The gel member 54 is disposed at least partially within the vibrating member cavity 52 of the vibrating member 50 against the vibrating member 50. The gel member 54 permanently retains the curved shape of the vibrating member 50 while disposed within the vibrating member cavity 52 of the vibrating member 50. The curved shape of the gel member 54 may comprise a hemispherical shape, an elliptical shape, or another curved shape. The gel member 54 may comprise a diameter 54a ranging between 3 to 9 inches (~8 to 23 centimeters). In one embodiment, the curved shape of the gel member 54 may comprise a radius of curvature 54b of up to one-half of the diameter 44b of the housing member 44. In a preferred embodiment, the diameter 54a is 5 inches (~12.7 cm) and the radius of curvature 54b is 2.5 inches (~6.35 cm). In another embodiment, the curved shape of the gel member 54 may comprise a radius of curvature 54b ranging between 1.5 to 4.5 inches (~4 to 12 centimeters). In other embodiments, the size, the shape, or the curvature of the gel member 54 may vary. The gel member 54 may be made of a material such as agar gel but in other embodiments may be made of a wide variety of tissue mimicking materials such as bovine gel, agarose gel, silicone gel, or any other tissue mimicking material.

The longitudinal waves 36 delivered by the tube 32 via the elbow joint 33 into the housing member cavity 46 pass through the vibrating member 50, into the vibrating member cavity 52, through the gel member 54, through the cover member 42, are converted at the boundary 56 between the passive acoustic driver 34 and the patient 14 into shear waves 38 via mode conversation, and the shear waves 38 are then transmitted into the patient 14 towards the area of interest 12 from a normal 60 to a point of least pressure intensity 62 at a diverging angle 58 ranging between 24 to 36 degrees. In other embodiments, the diverging angle 58 may vary. The system 10 of FIG. 1 may be used to take MRI images of the area of interest 12 of the patient 14 to capture the shear waves 38 transmitted into the area of interest 12 in order to determine a condition or property of the area of interest 12 to allow a physician to determine and diagnose the condition or a disease of the area of interest 12 based on the determined condition or properties.

Figure 4:
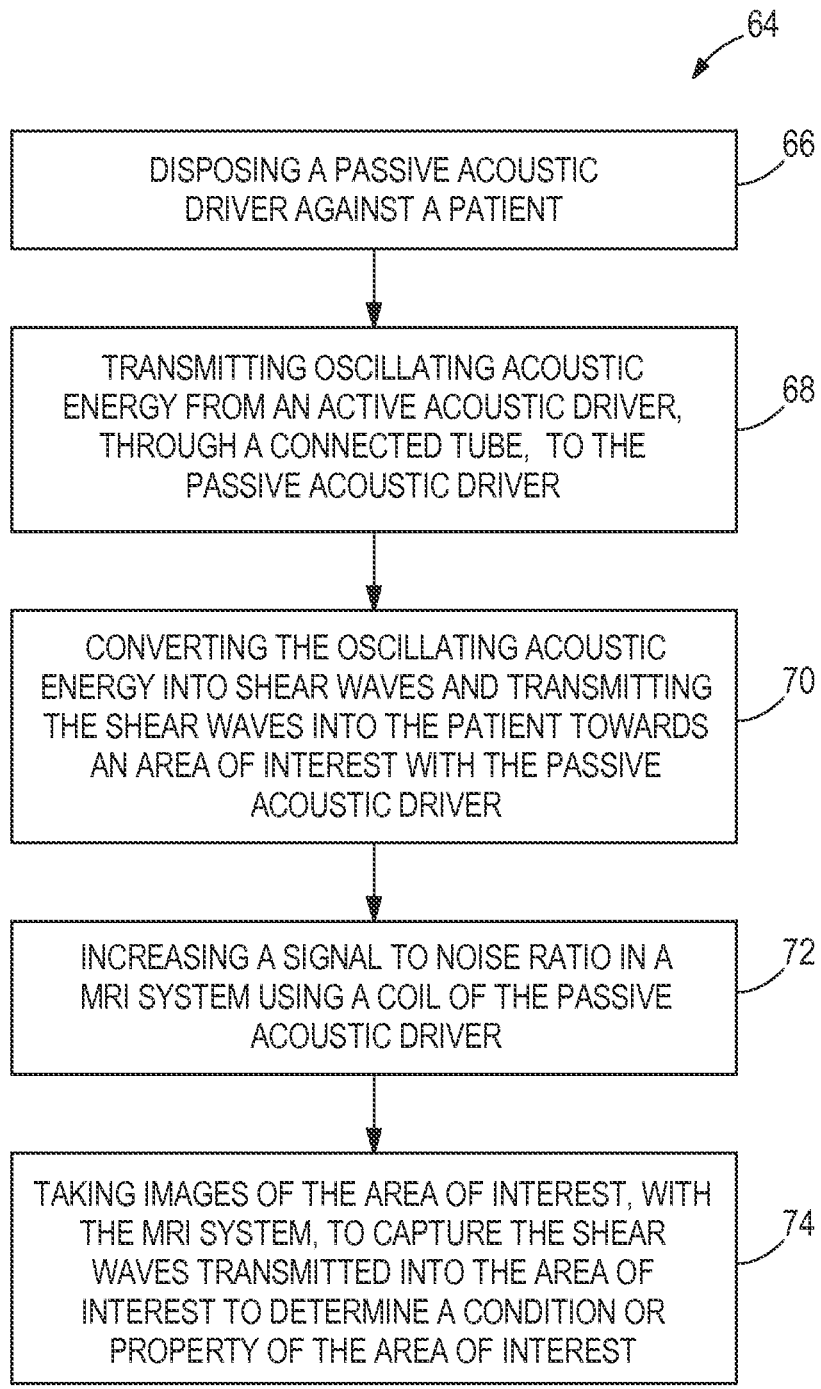
FIG. 4 is a flowchart illustrating one embodiment of a method of transmitting shear waves into a patient for magnetic resonance elastography.

FIG. 4 is a flowchart illustrating one embodiment of a method 64 of transmitting shear waves into a patient for magnetic resonance elastography. The method 64 may utilize the system 10 of FIG. 1. In step 66, a passive acoustic driver is disposed against a patient. The passive acoustic driver may comprise any of the embodiments disclosed herein. In step 68, oscillating acoustic energy is transmitted from an active acoustic driver, through a connected tube, to the passive acoustic driver disposed against the patient. The active acoustic driver may comprise any of the embodiments herein. The transmitted oscillating acoustic energy may comprise a frequency ranging between 40 to 100 Hz. In other embodiments, the frequency may vary.

In step 70, the oscillating acoustic energy is converted into shear waves and the shear waves are transmitted into the patient towards an area of interest with the passive acoustic driver. The shear waves may be transmitted into the patient towards the area of interest at a diverging angle from a normal to a point of least pressure intensity ranging between 24 to 36 degrees. In other embodiments, the diverging angle may vary. In step 72, a coil of the passive acoustic driver may increase a signal to noise ratio in a MRI system taking images of an area of interest of the patient. In step 74, the MRI system takes images of the area of interest to capture the shear waves transmitted into the area of interest in order to determine a condition or property of the area of interest to allow a physician to determine and diagnose the condition or a disease of the area of interest based on the determined condition or properties.

It has been discovered that the use of a curved passive acoustic driver better penetrates shear waves into a patient towards the area of interest allowing a physician to better determine and diagnose the condition or a disease of the area of interest based on the determined condition or properties. Modeling was done with the K-Wave Toolbox (compatible with MATLAB) to compare the results of using an existing flat passive acoustic driver versus using a curved passive acoustic driver by simulating pressure fields of different transducers which varied in size and shape. Simulations were run assuming a source frequency (acoustic wave frequency) of 60 Hz, and speed of 1540 m/s (speed of sound in tissue). These pressure field simulations were used to calculate the diverging angle of the waves, calculated as the angle away from the normal to the point of least pressure intensity, which describes the "blind zone" for the passive acoustic drivers. The blind zone is the area where minimal shear wave propagation occurs. It was discovered that as the diverging angle decreases, there is more shear wave propagation medially, producing a better sound image especially at greater depths.

Figure 5:
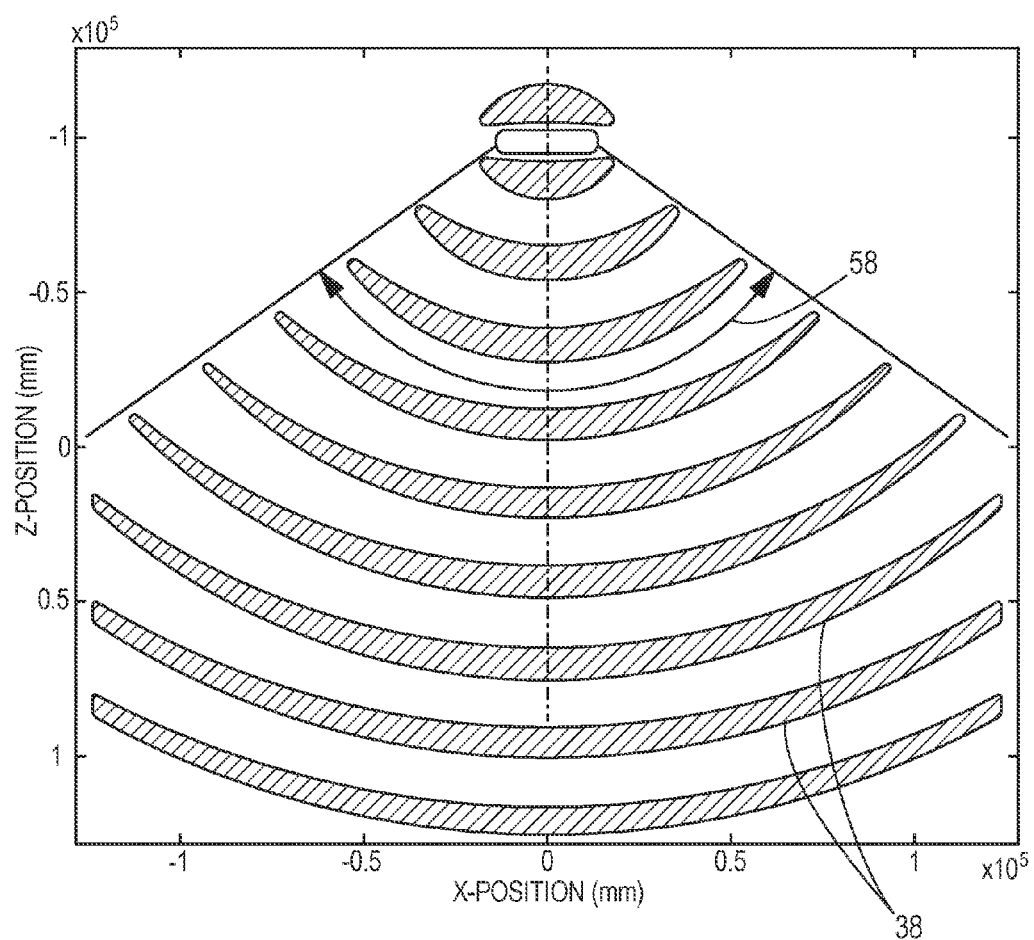
FIG. 5 illustrates a pictorial illustration of the shear wave propagation resulting from the use of one embodiment of an existing flat passive acoustic driver.

FIG. 5 illustrates a pictorial illustration of the shear wave propagation resulting from the use of one embodiment of an existing flat passive acoustic driver. As shown in FIG. 5, there is a large diverging angle 58 leading to a large blind zone and the shear wave 38 propagation is poor. It is noted that in MRE the propagation of the shear waves is critical. The shear waves are at their maximum where longitudinal compression waves are at their minimum. Thus, while there is a large amount of wave propagation directly under the flat passive acoustic driver of FIG. 5, these are in fact longitudinal waves which negate the shear waves and create the large diverging angle as they can only be imaged at the very edges of the cone these longitudinal waves create.

Figure 6:
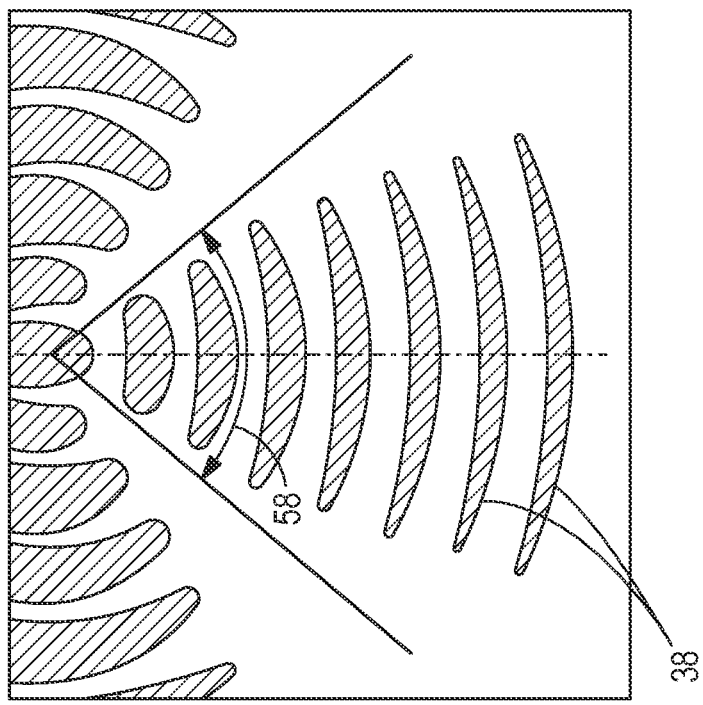
FIG. 6 illustrates a pictorial illustration of the shear wave propagation resulting from the use of one embodiment of a curved passive acoustic driver.

FIG. 6 illustrates a pictorial illustration of the shear wave propagation resulting from the use of one embodiment of a curved passive acoustic driver having a vibrating member which is 19 inches (~49 cm) in diameter. As shown in FIG. 6, there is a much smaller diverging angle 58 leading to a much smaller blind zone for the curved passive acoustic driver of FIG. 6 than for the flat passive acoustic driver of FIG. 5, and the shear wave propagation 38 for the curved passive acoustic driver is much improved over that of the flat passive acoustic driver.

Figure 7:
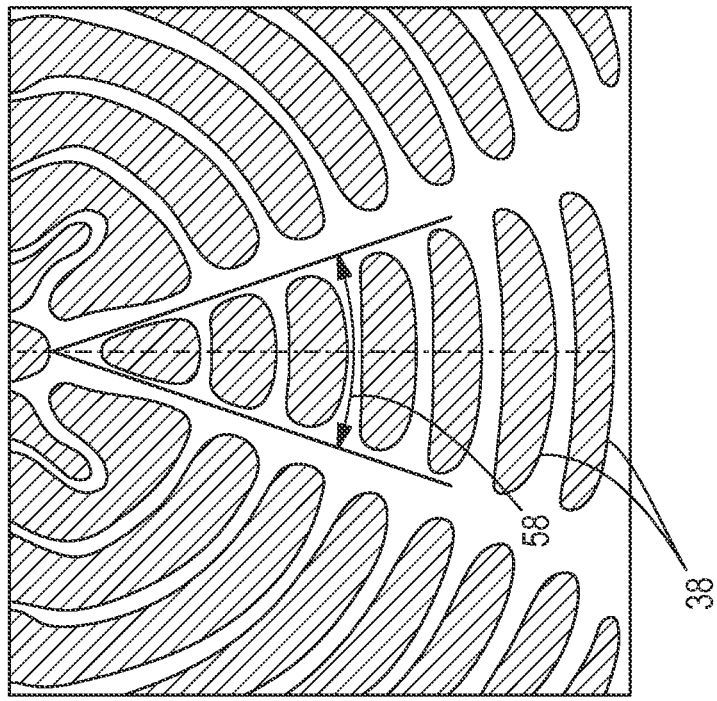
FIG. 7 illustrates a pictorial illustration of the shear wave propagation resulting from the use of another embodiment of a curved passive acoustic driver.

FIG. 7 illustrates a pictorial illustrate of the shear wave propagation resulting from the use of another embodiment of a curved passive acoustic driver having a vibrating member which is 25 inches (~63.5 cm) in diameter. As shown in FIG. 7, there is an even smaller diverging angle 58 leading to a much smaller blind zone for the curved passive acoustic driver of FIG. 7 than for the curved passive acoustic driver of FIG. 6, and the shear wave propagation 38 for the curved passive acoustic driver of FIG. 7 is much improved over that of the curved passive acoustic driver of FIG. 6. This demonstrates that as the size and shape of the vibrating member of the curved passive driver changes the diverging angle and the shear wave propagation also changes.

Figure 8:
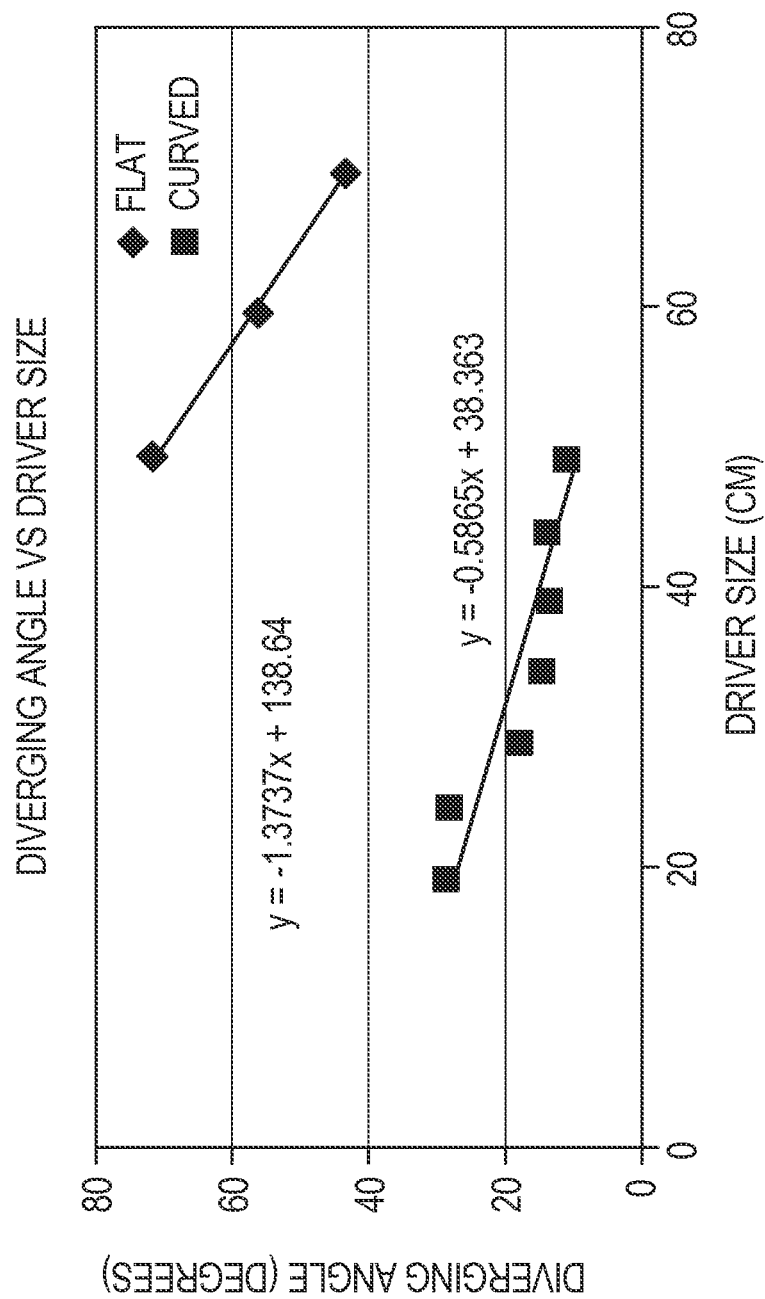
FIG. 8 illustrates a graph plotting driver size on the X axis and diverging angle on the Y axis for both a flat passive acoustic driver and a curved acoustic passive driver.

FIG. 8 illustrates a graph plotting driver size on the X axis and diverging angle on the Y axis for both a flat passive acoustic driver and a curved acoustic passive driver. FIG. 8 establishes that increased driver size decreases the diverging angles, that curved passive acoustic drivers significantly decrease the diverging angle of longitudinal waves over flat passive acoustic drivers, and that curved passive drivers are less sensitive to changes in driver sizes, and therefore allow for the use of a smaller curved passive driver while still maintaining a relatively small diverging angle. These conclusions were supported by mode conversion and near and far field propagation theories using MATLAB simulations. From the above findings, it is clear that flat passive acoustic drivers create large, planar longitudinal waves which create blind zones that increases in size with depth in the tissue, as the shear waves used to create the elastograms are of smaller magnitude and thus cannot be seen where the longitudinal waves are maximized.

On the other hand, as demonstrated—above, use of curved acoustic passive drivers converges the longitudinal waves, thereby decreasing the size of the blind zones and increasing the depth of penetration of the shear waves and thus the imaging capabilities. Use of curved acoustic passive drivers allows for elastrogram imaging of greater variety and depth of tissues and organs, including those other than the liver such as the pancreas, ovaries, and other body tissues and organs, using MRE technology allowing for quantification of stiffness therein.

Testing in three tissue-mimicking phantoms which were created with bovine ovaries inserted in agar at varying depths has revealed that the current flat passive acoustic drivers create waves that only consistently penetrate body tissue in a patient up to 6 centimeters deep. This is due to wave attenuation within the body tissue leading to a significant amount of kinetic energy being lost. As tissue depth is increased, the wave attenuation is increased leading to poor signal-to-noise ratio in the images of small, deep organs. On the other hand, this same testing has revealed that the use of curved acoustic passive drivers provides clinically relevant shear wave penetration up to 13 centimeters deep in a patient's body tissue. This is a drastic difference which allows the diagnosis and detection of cancerous tissues and other disease states in ovaries, kidneys, the pancreas, and in other body parts thereby reducing the need for invasive and costly biopsies.

Use of curved passive acoustic drivers will improve the reliability of imaging of the liver in cases such as obese patients, and in patients with high levels of bowel gases, and in other cases where wave attenuation is encountered with flat passive acoustic drivers. Moreover, use of curved passive acoustic drivers will increase the ability to diagnose conditions such as polycystic ovary syndrome (PCOS), ovarian cancer, chronic pancreatitis, and pancreatic cancer, in addition to diagnosing normal aging of the ovary, premature ovarian failure, idiopathic infertility which may be due to stiffness of ovarian tissue, or other conditions or diseases. PCOS is an extremely common disease with unknown etiology, and no specific means of diagnosis. Doctors must currently diagnose by exclusion; that is, they must weigh various factors such as the patient's medical history, the presence of certain symptoms, physical and pelvic examinations, blood tests for hormones, and a pelvic ultrasound before deciding which of a myriad of conditions applies, one of which is PCOS. The pelvic ultrasound is the only exam that uses imaging, yet the thicker ovaries that it attempts to detect are not present in many cases, and require use of an invasive trans-vaginal transducer. This is not only uncomfortable but often is also unacceptable for use in younger females who are a common demographic for screening. None of the above current methods allow for detection of the stiffness of the ovarian tissue, which may be the cause of the condition per recent studies.

The use of curved passive acoustic drivers to detect PCOS or to detect other diseases or conditions such as diagnosing normal aging of the ovary, premature ovarian failure, idiopathic infertility which may be due to stiffness of ovarian tissue, or other conditions or diseases, is a substantial improvement over existing methods of detection. Moreover, the use of curved passive acoustic drivers to detect stiffness in varying tissue and organs of the patient may lead to improved ability to diagnose cancer in these tissues, which is currently a challenging task due to risks associated with deep tissue biopsies and difficulty of imaging these tissues. Optimizing MRE for use in deeper organs through the use of curved passive acoustic drivers will allow for easier detection of rigid cancerous tumors therein, replacing the need for invasive diagnosing procedures such as biopsies.

It should be understood, of course, that the foregoing relates to exemplary embodiments of the disclosure and that modifications may be made without departing from the spirit and scope of the disclosure as set forth in the following claims.

We claim:

1. A passive acoustic driver comprising:
a housing member comprising a housing member cavity;
a vibrating member disposed at least partially within the housing member cavity, wherein the vibrating member permanently retains a curved shape while disposed within the housing member cavity; and
(1) a coil wrapped around the housing member; or (2) a cover member disposed over and attached to the housing member, the vibrating member disposed between the housing member and the cover member, the cover member covering an end of the housing member and an end of the vibrating member.

2. The passive acoustic driver of claim 1 wherein the passive acoustic driver is configured to transmit shear waves at a diverging angle from a normal to a point of least pressure intensity ranging between 24 and 36 degrees.

3. The passive acoustic driver of claim 1 further comprising a gel member disposed at least partially within a vibrating member cavity of the vibrating member.

4. The passive acoustic driver of claim 3 wherein the gel member permanently retains the curved shape while disposed within the vibrating member cavity.

5. The passive acoustic driver of claim 1 wherein the curved shape comprises a hemisphere.

6. The passive acoustic driver of claim 5 wherein the vibrating member comprises a diameter ranging between 3 to 9 inches.

7. The passive acoustic driver of claim 1 wherein the curved shape is elliptical.

8. The passive acoustic driver of claim 1 wherein the curved shape comprises a radius of curvature of up to one-half of a diameter of the housing member.

9. The passive acoustic driver of claim 1 wherein the curved shape comprises a radius of curvature ranging between 1.5 to 4.5 inches.

10. The passive acoustic driver of claim 1 wherein the passive acoustic driver includes the cover member disposed over and attached to the housing member, the vibrating member disposed between the housing member and the cover member, the cover member covering the end of the housing member and the end of the vibrating member.

11. The passive acoustic driver of claim 10 further comprising a gel member disposed at least partially within a vibrating member cavity of the vibrating member, wherein the cover member is disposed against and covers the gel member.

12. The passive acoustic driver of claim 1 further comprising an air tight seal between the housing member and the vibrating member with air disposed between the housing member and the vibrating member.

13. The passive acoustic driver of claim 1 wherein the passive acoustic driver includes the coil wrapped around the housing member.

14. An acoustic driver system comprising:
an active acoustic driver which is configured to produce oscillating acoustic energy;
a passive acoustic driver acoustically connected to the active acoustic driver which is configured to receive the oscillating acoustic energy and to convert it into shear waves, the passive acoustic driver comprising: a housing member having a housing member cavity; a vibrating member disposed at least partially within the housing member cavity, wherein the vibrating member permanently retains a curved shape while disposed within the housing member cavity; and (1) a coil wrapped around the housing member; or (2) a cover member disposed over and attached to the housing member, the vibrating member disposed between the housing member and the cover member, the cover member covering an end of the housing member and an end of the vibrating member.

15. The acoustic driver of clam 14 wherein the passive acoustic driver is configured to transmit the shear waves at a diverging angle from a normal to a point of least pressure intensity ranging between 24 and 36 degrees.

16. The acoustic driver system of claim 14 wherein the passive acoustic driver further comprises a gel member disposed at least partially within a vibrating member cavity of the vibrating member.

17. The acoustic driver system of claim 16 wherein the gel member permanently retains the curved shape while disposed within the vibrating member cavity of the passive acoustic driver.

18. The acoustic driver system of claim 14 wherein the curved shape comprises a hemisphere.

19. The acoustic driver system of claim 18 wherein the vibrating member comprises a diameter ranging between 3 to 9 inches.

20. The acoustic driver system of claim 14 wherein the curved shape is elliptical.

21. The acoustic driver system of claim 14 wherein the curved shape comprises a radius of curvature of up to one-half of a diameter of the housing member.

22. The acoustic driver system of claim 14 wherein the curved shape comprises a radius of curvature ranging between 1.5 to 4.5 inches.

23. The acoustic driver system of claim 14 wherein the passive acoustic driver includes the cover member disposed over and attached to the housing member, the vibrating member disposed between the housing member and the cover member, the cover member covering the end of the housing member and the end of the vibrating member.

24. The acoustic driver system of claim 23 wherein the passive acoustic driver further comprises a gel member disposed at least partially within a vibrating member cavity of the vibrating member, the cover member disposed against and covering the gel member.

25. The acoustic driver system of claim 14 wherein the passive acoustic driver further comprises an air tight seal between the housing member and the vibrating member with air disposed between the housing member and the vibrating member.

26. The acoustic driver system of claim 14 wherein the passive acoustic driver includes the coil wrapped around the housing member.

27. The acoustic driver system of claim 14 further comprising a tube acoustically connecting the active acoustic driver to the passive acoustic driver.

28. A method of transmitting shear waves into a patient for magnetic resonance elastography comprising:
disposing a passive acoustic driver against a patient, the passive acoustic driver comprising: a housing member having a housing member cavity; a vibrating member disposed at least partially within the housing member cavity, the vibrating member permanently retaining a curved shape while disposed within the housing member cavity; and (1) a coil wrapped around the housing member; or (2) a cover member disposed over and attached to the housing member, the vibrating member disposed between the housing member and the cover member, the cover member covering an end of the housing member and an end of the vibrating member;
transmitting oscillating acoustic energy from an active acoustic driver to the passive acoustic driver disposed against the patient; and
converting the oscillating acoustic energy into shear waves and transmitting the shear waves into the patient with the passive acoustic driver to conduct magnetic resonance elastography.

29. The method of claim 28 wherein the passive acoustic driver further comprises a gel member disposed at least partially within a vibrating member cavity of the vibrating member.

30. The method of claim 29 wherein the gel member permanently retains the curved shape while disposed within the vibrating member cavity of the passive acoustic driver.

31. The method of claim 28 wherein the curved shave comprises a hemisphere.

32. The method of claim 31 wherein the vibrating member comprises a diameter ranging between 3 to 9 inches.

33. The method of claim 28 wherein the curved shape is elliptical.

34. The method of claim 28 wherein the curved shape comprises a radius of curvature of up to one-half of a diameter of the housing member.

35. The method of claim 28 wherein the curved shape comprises a radius of curvature ranging between 1.5 to 4.5 inches.

36. The method of claim 28 wherein the passive acoustic driver includes the cover member disposed over and attached to the housing member, the vibrating member disposed between the housing member and the cover member, the cover member covering the end of the housing member and the end of the vibrating member.

37. The method of claim 36 wherein the passive acoustic driver further comprises a gel member disposed at least partially within a vibrating member cavity of the vibrating member with the cover member being disposed against and covering the gel member.

38. The method of claim 28 wherein the passive acoustic driver further comprises an air tight seal between the housing member and the vibrating member with air disposed between the housing member and the vibrating member.

39. The method of claim 28 wherein the passive acoustic driver includes the coil wrapped around the housing member.

40. The method of claim 39 further comprising the coil increasing a signal to noise ratio in a magnetic resonance imaging system taking images of the patient.

41. The method of claim 28 wherein the transmitted oscillating acoustic energy comprises a frequency ranging between 40 to 100 Hz.

42. The method of claim 28 wherein the transmitted shear waves are transmitted into the patient at a diverging angle from a normal to a point of least pressure intensity ranging between 24 and 36 degrees.

43. The method of claim 28 further comprising taking images of the patient using a magnetic resonance imaging system.

44. The method of claim 28 wherein the transmitting the oscillating acoustic energy from the active acoustic driver to the passive acoustic driver comprises transmitting the oscillating acoustic energy through a tube connected between the active acoustic driver and the passive acoustic driver.

* * * * *